United States Patent [19]

Schlossman

[11] 4,356,315

[45] Oct. 26, 1982

[54] CARBOXYPHENYLALKANOIC ACIDS AND LOWER ALKYL ESTERS THEREOF

[75] Inventor: Irwin S. Schlossman, Cincinnati, Ohio

[73] Assignee: Emery Industries, Inc., Cincinnati, Ohio

[21] Appl. No.: 245,466

[22] Filed: Mar. 20, 1981

[51] Int. Cl.³ .................. C07C 69/612; C07C 69/773; C07C 55/28
[52] U.S. Cl. .................................... 560/81; 562/489; 260/410.9 R; 260/413
[58] Field of Search ......................... 560/81; 562/489; 260/410.9 R, 413

[56] References Cited

U.S. PATENT DOCUMENTS 4,232,042  11/1980  Campbell et al. .................... 560/81

*Primary Examiner*—Natalie Trousof
*Assistant Examiner*—Vera C. Clarke
*Attorney, Agent, or Firm*—Kenneth D. Tremain

[57] ABSTRACT

Carboxyphenylalkanoic acids, and lower alkyl esters thereof, are described. These novel compounds are obtained by the non-classical oxidation of methylphenylalkanoic acids.

9 Claims, No Drawings

CARBOXYPHENYLALKANOIC ACIDS AND LOWER ALKYL ESTERS THEREOF

BACKGROUND OF THE INVENTION

1. Field of the Invention

The invention relates to novel dicarboxylic acids and, more specifically, to carboxyphenylalkanoic acids, and lower alkyl esters thereof.

2. General Description of the Prior Art

Liquid polycarboxylic acids are known and the utility of such products as curing agents for liquid epoxy systems is equally well recognized. For example, a liquid $C_{21}$ acid of the formula

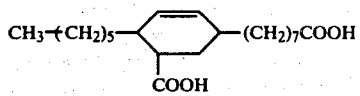

is obtained by the reaction of acrylic acid and linoleic acid in accordance with the process of U.S. Pat. No. 3,899,476. Useful high molecular weight liquid dicarboxylic acids can also be obtained by the polymerization of olefinically unsaturated fatty acids. Such polymeric fatty acids and processes for their preparation are described in U.S. Pat. Nos. 2,973,219 and 2,955,121. $C_{36}$ dimer acids and $C_{54}$ trimer acids are commercially produced by the polymerization of oleic acid, linoleic acid or mixtures thereof, e.g. tall oil fatty acids. The use of polycarboxylic acids of the above types in epoxy systems is disclosed in U.S. Pat. Nos. 3,268,477 and 4,098,735.

Since the particular carboxylic acid curing agent used can significantly affect the physical properties (chemical resistance, flexibility, shrinkage, adhesion, etc.) of the resulting cured resin and the cure rate, depending on the particular epoxy material being cured and whether other reactive monomers are present, new liquid polycarboxylic acids are constantly being sought for this purpose and for other uses.

SUMMARY OF THE INVENTION

The novel carboxyphenylalkanoic acids of this invention have the formula

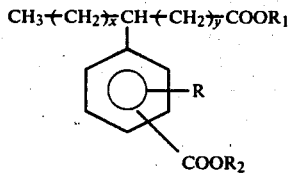

wherein $R_1$ and $R_2$ are hydrogen or a $C_{1-4}$ alkyl group, R is hydrogen, an alkyl group having 1 to 4 carbon atoms or a carboxyl group and x and y are integers such that $x+y$ equals from 5 to 23. In a more preferred embodiment of this invention R, $R_1$ and $R_2$ are hydrogen or methyl and the sum of x and y is an integer from 8 to 19. Especially useful liquid products of this invention are carboxyphenylstearic acid, carboxyphenylundecanoic acid, carboxyphenyldocosanoic acid and their methyl esters.

DETAILED DESCRIPTION

In accordance with this invention novel liquid carboxyphenylalkanoic acids and their lower alkyl esters are provided. The polycarboxylic acids are obtained by oxidation of the corresponding methylphenylalkanoic acids.

The carboxyphenylalkanoic acids of this invention are useful curing and flexibilizing agents for epoxy resins and can be utilized alone or in combination with other curing agents. Most generally, they are utilized in an epoxy ester coating system to impart desirable properties thereto and to improve the overall performance characteristics of the resulting cured resin. For example, the flexibility and hydrophobicity of epoxy coatings can be enhanced by the utilization of the carboxyphenylalkanoic acids of this invention. This makes it possible to obtain epoxy coatings having a good balance of hardness and flexibility and which exhibit improved chemical and hot-water resistance.

Additionally, the carboxyphenylalkanoic acids and their esters can be utilized in other applications where polymeric fatty acids (esters) and $C_{21}$ organic acids (esters) obtained from the addition of acrylic acid and linoleic acid are typically employed. For example, they may be utilized in the production of alkyd resins and alkyd oils useful as paint vehicles. They may also be utilized for the preparation of polyesters, polyamides and polyurethanes. In addition to esters and half-esters of these acids other derivatives such as salts, half-salts, amides, half-amides, alkanolamides, mixed amide salts, ethoxylated derivatives and the like can also be prepared and find utility in a variety of applications. Diesters of the dicarboxylic acids and higher alcohols, such as 2-ethylhexanol and tridecyl alcohol, typically exhibit low volatility and can be used as plasticizers and as lubricants.

The carboxyphenylalkanoic acids correspond to the formula

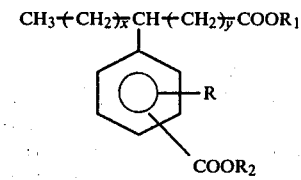

wherein $R_1$ and $R_2$ are the same or different and are selected from the group consisting of hydrogen or a $C_{1-4}$ alkyl group, R is hydrogen, an alkyl group having 1 to 4 carbon atoms or a carboxyl group and x and y are integers such that $x+y$ equals from 5 to 23. In an especially useful embodiment of this invention R, $R_1$ and $R_2$ are hydrogen or methyl and $x+y$ equals from 8 to 19. Carboxyphenylstearic acid, carboxyphenylundeanoic acid and carboxyphenyldocosanoic acid and the methyl esters of these acids are particularly advantageous products of this invention.

The carboxyphenylalkanoic acids are high-boiling liquids and are obtained from the corresponding methyl-substituted phenylalkanoic acid, e.g. tolylstearic acid, tolylundecanoic acid and tolyldocosanoic acid, using known non-classical catalytic oxidation procedures wherein the methyl group on the benzene ring is preferentially oxidized in the presence of other groups also present on the ring. Such a non-classical oxidation procedure using cobalt (II) acetate as the catalyst is described by Onopchenko et al. in J. Org. Chem., Vol. 37, No. 9 (1972). Co-catalyst systems such as those disclosed in U.S. Pat. No. 3,299,125 can also be utilized to obtain the carboxyphenylalkanoic acids. For the oxidation reaction, the methyl-substituted phenylalkanoic acid is typically combined with the catalyst in a carboxylic solvent, such as acetic acid, propionic acid or butyric acid, pressured with oxygen (up to about 750 psig max.) and heated at a temperature in the range 80° C. to 130° C., more usually 90° C. to 115° C.

Conventional esterification procedures are employed to obtain the lower alkyl esters of the carboxyphenylalkanoic acids of this invention. In general, such processes involve contacting the acid and alcohol at a temperature of about 90° C. to 250° C., more usually in the range 100° C. to 200° C. It is not necessary that a catalyst be employed for the reaction, however, conventional esterification catalysts, such as p-toluene sulfonic acid and the like, can be used. It may also be advantageous to remove water formed during the reaction and the reaction may be carried out in an inert diluent.

The following examples serve to illustrate the invention more fully. In these examples all parts and percentages are expressed on a weight basis, except for the percent selectivity which is on a molar basis.

EXAMPLE I

Preparation of tolylstearic acid: Concentrated sulfuric acid (1470 gms; 15 moles) were charged to a glass reactor equipped with a condenser, mechanical stirrer, thermometer, and addition funnel and cooled to about 5° C. Toluene (1380 gms; 15 moles) was then added over a two hour period while maintaining the temperature below 10° C. When the addition of toluene was complete, 831 gms (3 moles) oleic acid was incrementally added over a period of two hours. The reaction mixture was maintained below 10° C. for ½ hour and then allowed to rise to room temperature with continued stirring for 2 hours. Tolylstearic acid (1118.6 gms; 86.1% crude yield; acid value 154) was recovered and vacuum distilled.

Preparation of carboxyphenylstearic acid: One-hundred and eight grams of the distilled tolylstearic acid was charged to a one-liter stirred Parr autoclave with 400 mls acetic acid and 50 gms cobalt (II) acetate. The reactor was sealed, heated to 105° C. and pressured with oxygen to 350 psig.

The reaction was heated for 6½ hours with periodic additions of oxygen to maintain the pressure at 350 psig. At the completion of the reaction, 98.5 grams crude product (amber liquid having an acid value of 263) was recovered. Gas chromatographic analysis showed the crude product to consist of 6.7% monobasic acids (myristic, palmitic and stearic), 42.5% unreacted tolylstearic acid and 50.5% carboxyphenylstearic acid. The carboxyphenylstearic acid was confirmed by nuclear magnetic resonance spectroscopy.

A portion of the carboxyphenylstearic acid recovered from the above reaction was converted to the dimethyl ester by contacting with a molar excess methanol in the presence of a small amount of p-toluene sulfonic acid catalyst. For the reaction, the temperature was maintained at about 100° C. and methanol was introduced below the surface of the reaction mixture. At the completion of the reaction, the reaction mixture was vacuum distilled using a short-path micro-distillation apparatus. The distillation cut collected at 216°–225° C. (0.1–0.2 mm Hg) contained greater than 75% of the dimethyl ester of carboxyphenylstearic acid—which was confirmed by nuclear magnetic resonance spectroscopic analysis. Similar results are obtained when ethanol, propanol or butanol are substituted in the above reaction.

EXAMPLE II

Tolylstearic acid was oxidized in accordance with the procedure described in Example I. For the reaction 54 gms tolylstearic acid, 400 mls acetic acid and 40 gms cobalt (II) acetate were used. The oxidation was conducted for six hours at 105° C. and 350 psig $O_2$. Sixty-seven percent conversion tolylstearic acid was achieved with 69.3% selectivity to the desired carboxyphenylstearic acid.

EXAMPLE III

The oxidation procedure of Example I was repeated except that only 40 gms cobalt (II) acetate was employed. Also, for this reaction 40 gms methylethyl ketone and 72 gms butane were charged to the reactor. Eighty percent conversion of the tolylstearic acid was achieved after only four hours reaction (105° C. and 350 psig $O_2$). Carboxyphenylstearic acid was obtained in 47.9% yield.

A portion of the crude product (acid value 271) was esterified with methanol using sulfuric acid catalyst to convert the dicarboxylic acid product to the methyl ester. Another portion of the carboxyphenylstearic acid was mixed with an equal weight of a low molecular weight liquid epoxy resin (diglycidyl ether of bisphenol A; epoxide equivalent 192). A small amount of triethylenetetramine catalyst was added and the mixture heated at 120°–130° C. to obtain a non-tacky polymer which exhibited good flexibility and low shrinkage.

EXAMPLE IV

In accordance with the general procedures described above m-xylene (1590 gms; 15 moles) was added dropwise to a mixture of 847 gms (3 moles) oleic acid and 1470 gms (15 moles) sulfuric acid. Upon work-up, 843.9 gms (69.5% yield) crude m-xylylstearic acid (acid value 140) was obtained. The m-xylylstearic acid was vacuum distilled and 108 gms of the distilled product (93+% m-xylylstearic acid) charged to an autoclave with 400 mls acetic acid and 40 gms cobalt (II) acetate. The reactor was pressurized with oxygen to 350 psig and heated at 150° C. for 6 hours after which time the acid value of the reaction mixture was 265, which is approximately the value calculated for oxidation of one of the methyl groups on the ring. Nuclear magnetic resonance spectroscopic analysis confirmed that the predominant product was 2-methyl-4-carboxyphenylstearic acid.

EXAMPLE V

Undecylenic acid (532 gms; 3 moles) was slowly added to 1470 gms (15 moles) sulfuric acid and 1380 gms (15 moles) toluene at a rate such that the temperature was maintained between 5°–8° C. The reaction mixture was quenched over ice and the toluene phase washed with a saturated solution of sodium chloride until the pH of the wash water was 4–5. Excess toluene was removed by evaporation and crude tolylundecanoic acid (acid value 197) recovered in 87.6% yield. The crude tolylundecanoic acid was distilled and 108 gms of the distilled product (acid value 203) charged to an autoclave with 400 mls acetic acid, 9.8 gms $Co(OAc)_2.4H_2O$ and 1.3 gms $ZrO(OAc)_2$. Oxidation was conducted at 105° C. and 350 psig $O_2$ for 6 hours. Selectivity to carboxyphenylundecanoic acid was 70.1% with 53.8% conversion of the tolylundecanoic acid.

EXAMPLE VI

Five-hundred grams molten erucic acid were slowly added to a mixture of 679 gms toluene and 723 gms concentrated sulfuric acid while maintaining the temperature below 10° C. Tolyldocosanoic acid (acid value 123) was obtained in 82% yield. Distilled tolyldocosanoic acid (108 gms), 400 mls acetic acid 9.8 gms Co(OAc)$_2$.4H$_2$O and 1.3 gms ZrO(OAc)$_2$ were then heated at 105° C. and 350 psi O$_2$ for six hours during which time the acid value increased from 127 to 207. The selectivity to the desired carboxyphenyldocosanoic acid was 64.4% at a tolyldocosanoic conversion of 53.7%.

I claim:

1. A compound having the formula

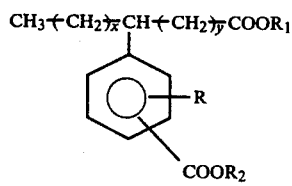

wherein
R represents hydrogen, a carboxyl group or a $C_{1-4}$ alkyl group;
R$_1$ and R$_2$ are the same or different and are each selected from the group consisting of hydrogen or $C_{1-4}$ alkyl; and
x and y are positive integers such that x+y equals from 5 to 23.

2. A compound of claim 1 wherein R, R$_1$ and R$_2$ are hydrogen or methyl.

3. A compound of claim 2 wherein x+y equals from 8 to 19.

4. The compound of claim 1 which is carboxyphenylstearic acid.

5. The compound of claim 1 which is the methyl ester of carboxyphenylstearic acid.

6. The compound of claim 1 which is carboxyphenylundecanoic acid.

7. The compound of claim 1 which is the methyl ester of carboxyphenylundecanoic acid.

8. The compound of claim 1 which is carboxyphenyldocosanoic acid.

9. The compound of claim 1 which is the methyl ester of carboxyphenyldocosanoic acid.

* * * * *